(12) United States Patent
Matear et al.

(10) Patent No.: US 9,707,561 B2
(45) Date of Patent: Jul. 18, 2017

(54) ASSAY FLUID DELIVERY SYSTEM (71) Applicant: Randox Laboratories Ltd., Antrim (GB)

(72) Inventors: Jonathan Matear, Antrim (GB); Robson Pang, Antrim (GB); Stuart Jackson, Antrim (GB); David Sloan, Antrim (GB)

(73) Assignee: Randox Laboratories Ltd., Crumlin (IE)

( * ) Notice: Subject to any disclaimer, the term of this patent is extended or adjusted under 35 U.S.C. 154(b) by 0 days.

(21) Appl. No.: 15/038,024

(22) PCT Filed: Nov. 19, 2014

(86) PCT No.: PCT/GB2014/053422
§ 371 (c)(1),
(2) Date: May 19, 2016

(87) PCT Pub. No.: WO2015/075447
PCT Pub. Date: May 28, 2015

(65) Prior Publication Data
US 2016/0296930 A1 Oct. 13, 2016

(30) Foreign Application Priority Data
Nov. 21, 2013 (GB) .................................. 1320542.2

(51) Int. Cl.
*G01N 35/10* (2006.01)
*G01N 35/04* (2006.01)
(Continued)

(52) U.S. Cl.
CPC ..... *B01L 3/50273* (2013.01); *B01L 3/502715* (2013.01); *B01L 3/527* (2013.01);
(Continued)

(58) Field of Classification Search
CPC ........... B01L 3/502715; B01L 3/50273; B01L 2200/027; B01L 2200/0621;
(Continued)

(56) References Cited

U.S. PATENT DOCUMENTS 3,948,605 A * 4/1976 Atwood .................... G01N 1/38
422/63
5,073,343 A 12/1991 Hukuhara et al.
(Continued)

FOREIGN PATENT DOCUMENTS

WO 2006043642 A1 4/2006

OTHER PUBLICATIONS

Price, Elizabeth, Search Report Under Section 17(5), European Patent Office, PCT/GB2014/053422, May 22, 2014.
(Continued)

*Primary Examiner* — Jennifer Wecker
(74) *Attorney, Agent, or Firm* — Gavrilovich, Dodd & Lindsey LLP (57) ABSTRACT

There is provided an assay fluid delivery system comprising an array of fluid reservoirs (62), each of which is selectively actuatable to deliver a respective fluid to a fluid channel structure; and a fluid delivery control system (50) comprising a plurality of reciprocally mounted actuators, each associated with a respective reservoir and being movable between a retracted position and an actuating position at which it causes fluid to be delivered from the corresponding reservoir, a plurality of cams (22) with different profiles mounted on a common, rotatable cam shaft (6), each cam being engaged with a respective one of the actuators whereby rotation of the cams causes movement of the corresponding actuators between the retracted and actuating positions, and a motor coupled to the cam shaft for rotating the cam shaft, wherein the cams are shaped relative to one
(Continued)

another so as to cause the corresponding actuators to actuate the reservoirs in a predetermined sequence and for predetermined respective times.

13 Claims, 5 Drawing Sheets (51) Int. Cl.
F04B 9/04 (2006.01)
B01L 3/00 (2006.01)
G01N 1/38 (2006.01)
G01N 35/00 (2006.01)

(52) U.S. Cl.
CPC ..... B01L 2200/027 (2013.01); B01L 2200/04 (2013.01); B01L 2200/0605 (2013.01); B01L 2200/0621 (2013.01); B01L 2200/10 (2013.01); B01L 2200/16 (2013.01); B01L 2300/0816 (2013.01); B01L 2300/123 (2013.01); B01L 2400/0478 (2013.01); B01L 2400/0481 (2013.01); B01L 2400/0487 (2013.01); F04B 9/042 (2013.01); G01N 35/00029 (2013.01); G01N 35/1002 (2013.01); G01N 2035/00148 (2013.01); G01N 2035/0486 (2013.01)

(58) Field of Classification Search
CPC ......... B01L 2200/04; B01L 2200/0605; B01L 2200/10; B01L 2200/16; B01L 2400/0487; G01N 35/1002; G01N 2035/0486; F04B 9/042
See application file for complete search history.

(56) References Cited

U.S. PATENT DOCUMENTS

| 5,374,395 | A | * | 12/1994 | Robinson | ............. | G01N 21/253 |
| | | | | | | 422/562 |
| 2002/0086417 | A1 | * | 7/2002 | Chen | .................... | B01L 3/5027 |
| | | | | | | 435/287.3 |
| 2008/0217246 | A1 | | 9/2008 | Benn et al. | | |
| 2010/0304986 | A1 | * | 12/2010 | Chen | ................ | B01L 3/502715 |
| | | | | | | 506/9 |
| 2012/0168305 | A1 | | 7/2012 | Hunter et al. | | |
| 2013/0210015 | A1 | * | 8/2013 | Williams | ................ | C12Q 1/68 |
| | | | | | | 435/6.12 |

OTHER PUBLICATIONS

Written Opinion of the International Searching Authority, European Patent Office, PCT/GB2014/053422.

* cited by examiner

ASSAY FLUID DELIVERY SYSTEM

The invention relates to an assay fluid delivery system, for example for carrying out one of an immunoassay, molecular, food or toxicology diagnostics assay.

A common approach to undertaking assays is to utilize so-called lab on chip and related technologies in which very small volumes of samples and reagents are processed by supplying them in a controlled manner through microfluidic channels to target locations where reactions can take place again in a controlled environment.

Fluid delivery is a critical function when using a microfluidic system for analysis. In some cases, pipettes can be used to delivery fluids, but these often introduce error as operational consistency depends on user experience.

U.S. Pat. No. 5,073,343 discloses a system that delivers fluids into channels by means of an open-topped reservoir into and out of which fluid can be fed. The top of each reservoir has a seal around its edge that forms a seal with a piston that is fitted into the top. When each piston is pushed into the respective reservoir, fluid is pushed out, each piston is then returned to its starting position by a spring.

Each piston is pushed into the reservoir by a cam. U.S. Pat. No. 5,073,343 discloses two sets of cams arranged in a single line. Each set of pistons is pushed into the respective reservoirs by a one of two distinct groups of cams that are all mounted on a single cam shaft. Which set of pistons is operated is determined by the direction in which the cam shaft is rotated. This is because the cam shaft has a clutch system that causes one group of cams to rotate when the cam shaft is rotated one way (e.g. clockwise), and causes the second group of cams to rotate when the cam shaft is rotated in the opposite direction (e.g. anti-clockwise). In this manner, each set of pistons is able to be operated independently of the other set of pistons.

Blister packs are often used to store the reagents required for an assay during transport and the fluid only undergoes transport when the blister is burst by some exertion of force on to it during the run of an assay. This can be achieved manually as described in US-A-2007/0263049 or by a stepper motor driven actuator such as described in WO-A-2010/091246 and US-A-2008/0217246. This solution requires that a single stepper motor be present over each blister pack so as to actuate and burst the blister, releasing fluid, at the required time.

Chambers moulded in to a card and filled with reagents have also been used as a fluid delivery system.

A means of releasing fluid from a chamber is disclosed in US-A-2012/0168305. This discloses a system with multiple fluid chambers. The fluid is released from each chamber by use of a pendently-controlled plunger. At one end of each pendently-controlled plunger there is a tip that is capable of being pushed against a chamber, the middle of each plunger is attached to a fulcrum around which the plunger is rotatable, and the other end of each plunger from the respective tip has a yoke that is fitted around a cam mounted on a cam shaft.

To push each tip against the respective chamber, the cam shaft is rotated by a motor thereby rotating the cam. This causes the yoke-end of the plunger to rise do to the profile of the cam, pushing the tip down against the respective chamber. As in U.S. Pat. No. 5,073,343, each plunger is operated independently by use of a clutch, which causes the relevant cam to rotate with the cam shaft in when the cam shaft is rotated in one direction (e.g. clockwise), and not when the cam shaft is rotated in the opposite direction (e.g. anti-clockwise).

Once a fluid is released from a chamber from whatever source, a form of pneumatics is often employed to drive the fluid along the required path. This requires an expensive, complex, noisy, pneumatic system consisting of many parts. Accuracy and precision of the delivery of volume is dependent on ambient air pressures and temperature. A complex control system, often based on electronics, is also required to control the initial release of the fluid and the pneumatics system.

In WO-A-2006/043842, a pump is used to push fluid along the required path. The pump comprises a cam shaft on which two identical elliptical cams are mounted with the cam shaft passing through each elliptical cam near one of the foci of each elliptical cam. Each cam is in contact with a roller located on the end of a ram. At an opposing end of each ram from the roller, there is a disc shaped piston, which has the same area as the internal area of a cylinder in which it is held.

Each cylinder has an inflow and an outflow channel, each of which has a one-way valve. The inflow channels are supplied by a single fluid supply and the outflow channels pass into a single fluid channel. Each piston is capable of reciprocal motion along the length of the cylinder pushing fluid out of the cylinder through the outflow channel, and pulling fluid into the cylinder through the inflow channel as the piston moves down and up the cylinder respectively.

The downward motion of the pistons is caused by rotation of the cams pushing the pistons up their respective cylinders; and the upward motion of the piston is caused by a pneumatic system pushing the piston back down the respective cylinder. In WO-A-2006/043842, the cams are orientated so that they are 180 degrees out of phase. As such, when one piston is in a fully extended position due to urging by the respective cam, the other piston is in a fully retracted position due to urging by the pneumatic system. Having identical cams that are 180 degrees out of phase ensures that the pump maintains a consistent pressure when the pump is operated.

A further problem with the traditional solution to transport fluid in microfluidic devices is that the supporting engineering is relatively bulky, noisy, costly, hot during use, complicated and is subject to reliability issues due to the many moving and heat producing parts. A creative method of dissipating heat is often required as the functionality of the technology depends on temperature and atmospheric pressure. An error boundary to the functionality of the fluid delivery system is therefore inherent. This affects the development and validation of the assay run on the analyser, further complicating the process.

In many applications, the available number of fluids on a card or blister pack is restricted by the size of the actuators and motors used to initially release the fluid and the footprint of the card.

There is therefore a need to provide a simpler control system for use in an assay fluid delivery system which avoids the problems mentioned above.

In accordance with a first aspect of the present invention, an assay fluid delivery system comprises an array of fluid reservoirs, each of which is selectively actuable to deliver a respective fluid to a fluid channel structure; and a fluid delivery control system comprising a plurality of reciprocally mounted actuators, each associated with a respective reservoir and being movable between a retracted position and an actuating position at which it causes fluid to be delivered from the corresponding reservoir, a plurality of cams with different profiles mounted on a common, rotatable cam shaft, each cam being engaged with a respective one of the actuators whereby rotation of the cams causes movement of the corresponding actuators between the retracted and actuating positions, and a motor coupled to the cam shaft for rotating the cam shaft, wherein the cams are shaped relative to one another so as to cause the corresponding actuators to actuate the reservoirs in a predetermined sequence and for predetermined respective times.

With this invention, we have developed a compact cam-based control system which is operated using a single motor such as a stepper motor thus reducing noise and expense. Furthermore, the control system can be constructed very accurately by suitable choosing the profiles of the cams to ensure that the same process is effected each time the control system is operated and to ensure that fluids are released from the reservoirs in the correct sequence and correct times and removes the risk of out-of-order fluid flow each time the control system is operated. This further removes the inaccuracies of the conventional pipette approach while providing statistical consistency for fluid delivery and maintaining the accuracy and precision required of an assay.

The compact cam actuated piston fluid delivery technology is scalable. This means that we can take advantage of the compactness of the control system in the horizontal plane to add more reagent storage to the card or other storage device to fit very complicated assay routines using many fluids without the card and medical device becoming large and unwieldy.

Only a single motor is used to drive the cam shaft reducing the size and complexity of the supporting electronics and reducing thermal/emc/noise emission.

The invention is not affected by atmospheric heat or pressure changes and is capable of delivering fluid with great accuracy and precision according to the shapes of the cam profiles and the capabilities of the motor in a wide range of atmospheric conditions, making Point of Care viable. Fluid flow-rates can also be scaled according to the speed of actuation in the motor. The order of fluid delivery for different reservoirs is set at the design stage of the control system thus reducing the risk of unintended fluid delivery to zero and making an automated assay procedure more reliable.

Further advantages include the fact that the actuation order cannot be altered, removing the risk of inaccurate fluid delivery entirely and making any automated set-pattern fluid delivery process more reliable.

In some examples, multiple fluids can be transported at the same time.

Accuracy and precision of any fluid delivery is maximized. The time to recover between full actuation runs is also negligible with this design.

Preferably, when actuated, the piston will remain in the down position until the end of the assay. This prevents unintended backflow/backwash along the microfluidic circuit and is achieved by suitably shaping the associated cam. The cam profiles can be shaped to achieve a variety of effects in addition simply to releasing fluid from a reservoir or chamber. For example, a cam may be shaped to cause increasing pressure to be applied to the corresponding reservoir after fluid commences flowing from that reservoir. This ensures that fluid continues to flow from the reservoir and there is no backflow. Preferably, the motor is adapted to operate continuously but in some cases could operate in an intermittent manner. The choice will depend on reaction times of the reagents and the distances they have to flow to appropriate targets.

In preferred examples, the cams are shaped so that after actuation, each actuator remains in its actuating position until the last actuator is actuated. This also helps to prevent fluid backflow.

Preferably, the fluid delivery control system comprises two lines of reciprocally mounted actuators in a rectilinear arrangement, wherein the cam shaft is located between the two lines so as to allow both lines of actuators to be engaged by the plurality of cams. This increases the number of actuators that can be engaged by cams mounted on a single cam shaft therefore minimising the increase in noise, complexity and expense when using a larger number of actuators (and corresponding number of fluid reservoirs). This also allows for efficient use of space by minimising the distance between adjacent actuators.

Conveniently, each actuator is urged towards its retracted position, for example by a spring. In this way, each actuator is urged against the corresponding cam and there is always contact between the two components. However, it would also be possible for other, more complex linkages to be provided between each actuator and cam.

Typically, the actuators are detachable so that they can be cleaned but also replaced with alternatives suited to the particular reservoirs in use.

Each fluid reservoir may have a barrier between the fluid contained in the respective fluid reservoir and the respective actuator so as to maintain a separation between the fluid held in the respective fluid reservoir and the respective actuator. This removes the possibility of (cross-)contamination when the fluid delivery control system is used with a different array of fluid reservoirs. As such, there is a reduced need to clean each actuator after each use.

Furthermore, by forming a barrier between fluid and actuator, there is less chance of leaking because of the motion of an actuator, and there is no chance of contamination between fluids because of foreign residue on the actuator. Such foreign residue could include fluid residue from other fluid delivery systems when using the fluid delivery control system with multiple sets of fluid reservoirs, or could be other material.

As has been mentioned above, the fluid reservoirs are typically provided in a blister pack and the actuator will crush a wall of a reservoir formed in a blister pack causing another part of the wall to rupture and allow fluid to flow out. However, the reservoirs could be formed by partially rigid chambers in which the actuator applies a force in a linear plane to manipulate a malleable elastic membrane that covers the top of an otherwise rigid fluid container. As the actuator is driven by a cam, the direction of force can be changed by 180°. This means that each individual actuator drives a fluid flow by application of force toward an exit port in the fluid container and if a number of actuators are combined together a pump is created. The motion of each actuator is timed to drive fluid along a set path. In this case, some actuators are directly associated with a fluid flow path and not a reservoir wall.

In a further option, the reservoirs are formed in fully rigid chambers. In these cases, the actuator acts upon a syringe-like plunger which is forced into the chamber.

In accordance with a second aspect of the present invention, we provide a fluid delivery control system for use in an assay fluid delivery system according to the first aspect of the invention, the fluid delivery control system comprising a plurality of reciprocally mounted actuators, each associated with a respective reservoir and being movable between a retracted position and an actuating position at which it causes fluid to be delivered from the corresponding reservoir, a plurality of cams with different profiles mounted on a common, rotatable cam shaft, each cam being engaged with a respective one of the actuators whereby rotation of the cams causes movement of the corresponding actuators between the retracted and actuating positions, and a motor coupled to the cam shaft for rotating the cam shaft, wherein the cams are shaped relative to one another so as to cause the corresponding actuators to move to the actuated position in a predetermined sequence and for predetermined respective times.

An example of an assay fluid delivery system according to the invention will now be described with reference to the accompanying drawings, in which.

Figure 2:
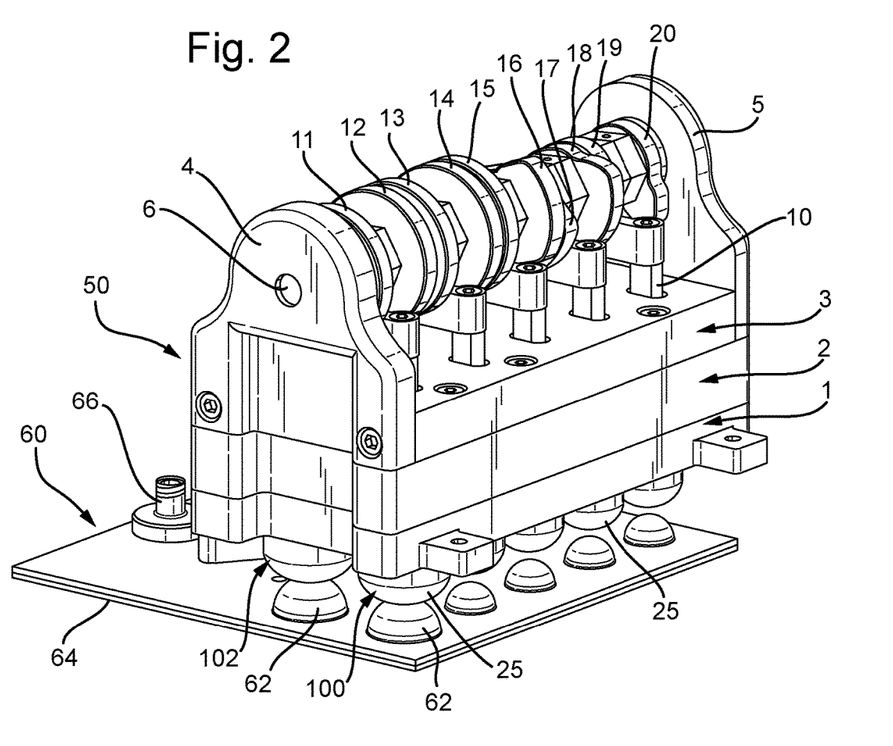
FIG. 2 is a perspective view of the assay fluid delivery system prior to actuation.

FIG. 2 illustrates the assay fluid delivery system in perspective form, the system comprising a fluid delivery control system 50 located above a blister pack 60. The blister pack has a number of fluid reservoirs formed in respective blisters 62 located in a two-dimensional array, there being ten blisters in all. The blister pack 60 further includes a fluid channel structure 64 bonded to the blister layer in a conventional manner.

Figure 6:
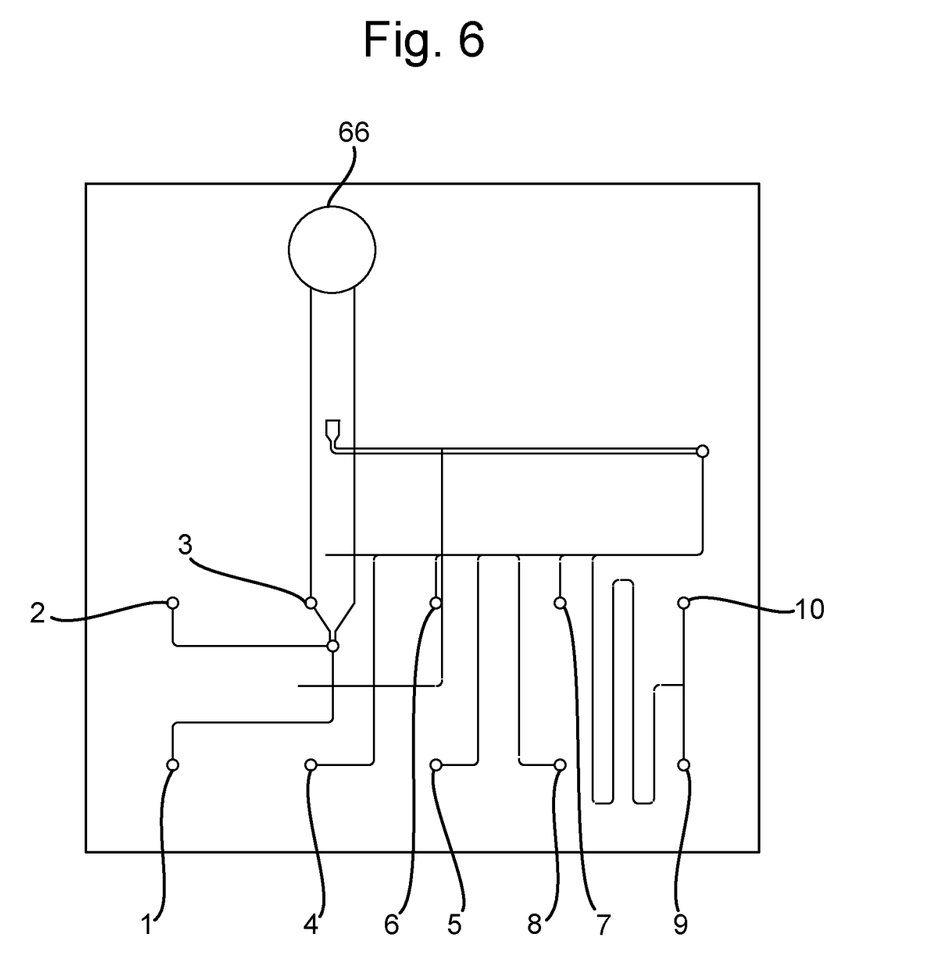
FIG. 6 illustrates the microfluidic channels linked to the blister reservoirs; and, FIG. 7 is an enlarged side view of a cam.

The fluid channel structure 64 is shown in more detail in FIG. 6. The blisters 62 are individually labelled 1-10 respectively while the fluid channels are shown by dashed lines "----". A sample to be analysed is supplied through an introduction port 66. The introduced sample passes through various fluid channels in a conventional manner and will be mixed with reagents ejected from the respective blisters in a conventional manner. An extraction port (not shown) is provided to enable fluid to be removed following completion of the analysis.

Located above the blisters 62 is the fluid delivery control system 50. This is shown in more detail in FIG. 1. The control system 50 comprises a lower bushing housing plate 1 on which is secured a spring locating plate 2 and an upper bushing housing plate 3. The plates 1-3 each have an array of ten bores aligned with respective blisters 62. Each set of aligned bores contains a piston or actuator assembly shown most clearly in FIG. 3. Each piston assembly comprises a piston rod 10, the upper end of which is secured to a piston connector 21 carrying a cam follower 22. The piston rod 10 extends through an upper bushing 8 located in the corresponding bore in the upper bushing housing plate 3, a compression spring 26 located in the corresponding bore in the spring locating plate 2 and a lower bushing 7 located in the lower bushing housing plate 1. The lower end of the piston rod 10 is secured to a piston 25 having a semi-spherical lower surface which engages the corresponding blister 62.

Figure 3:
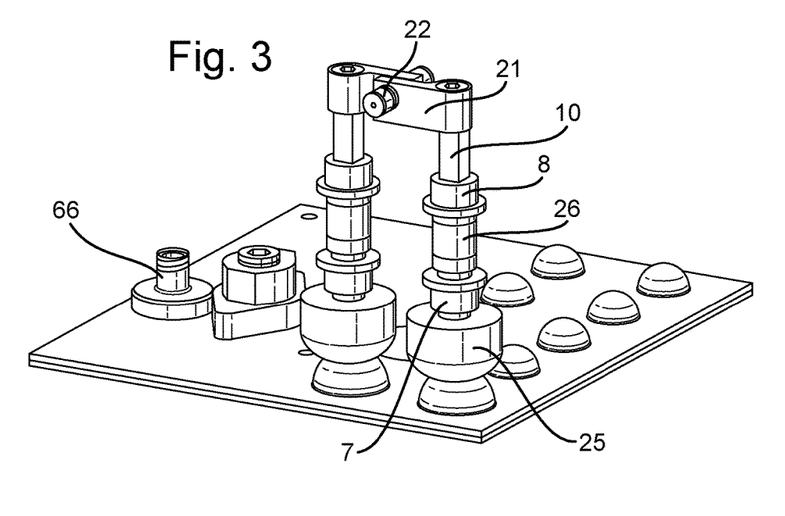
FIG. 3 illustrates two of the actuators of the control system shown in FIG. 2 but with other elements removed.

The piston 25 is detachable from the piston rod 10, for example via a screw thread, to allow it to be replaced by an alternative actuating head depending upon the function required.

In order to control actuation of the piston rods 10, a set of cams 11-20 mounted on a cam shaft 6 is located above the upper bushing housing plate 3, the cam shaft 6 being rotatably mounted to left and right housing plates 4,5 via bearings 9. A single cam is shown in more detail in FIG. 7.

The cam shaft 6 has a hexagonal cross-section corresponding to the hexagonal cross-section of bores 70 through the cams 11-20 (FIG. 7) so that the cams can be threaded onto the cam shaft 6 and be non-rotatable with respect to the cam shaft.

Figure 1:
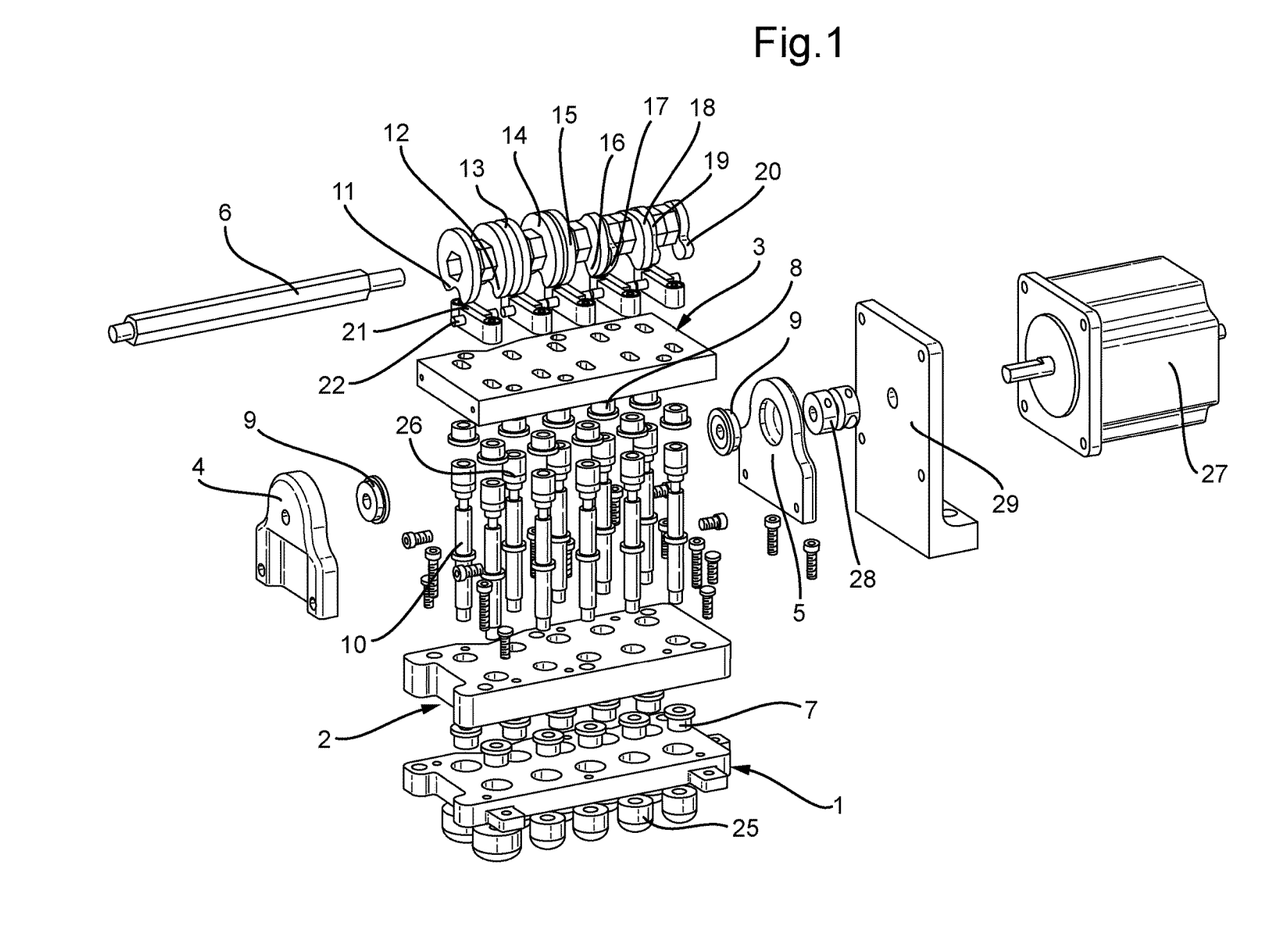
FIG. 1 is an exploded view of the fluid delivery control system of the assay fluid delivery system.

The end of the cam shaft 6 which passes through the plate 5 is coupled via a coupling 28 to a stepper motor 27 mounted on a support bracket 29.

The springs 26 urge the piston rods 10 into their retracted positions shown in FIGS. 2 and 3 in which little or no pressure is applied to the corresponding blisters 62 and in which the cam followers 22 are urged against the cams 11-20.

Typically, the cams 11-20 and cam followers 22 are made from stainless steel while the rest of the assembly is aluminium to reduce weight and costs.

When the stepper motor 27 is actuated, it rotates the cam shaft 6 which in turn rotates the cams 11-20. Each of the cams 11-20 engages a respective cam follower 22 and as the profile of each cam varies, the cam follower 22 moves in correspondence and this rotation movement is translated into linear movement of the respective piston rods 10. Typically, a linear movement of about 6 mm occurs.

It is worth noting that the aligned bores in the bushing housing plates 1, 3 and spring locating plate 2 form a cylindrical shape that each guides a respective piston rod in its linear movement. Due to the consistent alignment, this provides an accurate system for engaging with the blisters, and reduces wear on the parts caused by misalignment ensuring longevity of the parts. This is in contrast to the prior art which, as is disclosed in US-A-2012/0168305, uses a tip attached to the end of a plunger that is rockable around a fulcrum. Using such an arrangement may cause misalignment and wear as the plunger will rock according to the tolerances of the body causing the motion. This allows the movement of the tip to be influenced by the tolerances of the body causing the motion, instead of being guided along a predetermined path as is the case here.

In operation, the blister pack 60 with the fluid channel structure 64 is inserted under the control system 50 so that the blisters 62 are aligned with the respective pistons 25. The motor 27 is then activated so as to rotate the cam shaft and hence the cams 11-20. It can be seen in the drawings that the cams have different profiles 72 and thus as they rotate (anticlockwise in FIG. 7), each cam follower will undergo a different sequence of movements from the others with corresponding different movements of the attached piston shafts 10. As the diameter of a cam increases, the cam follower 22 urged against that cam will be depressed downwardly causing downward movement of the associated piston shaft 10 against the action of the compression spring 26. This will move the piston 25 downwardly as shown in FIGS. 4 and 5 thereby flexing or crushing the wall of the associated blister 62 and forcing another part of the blister (not shown) to rupture so that fluid is ejected into the underlying fluid channel structure.

During continued rotation of the cam shaft 6, while the diameter of the cam remains at its largest, the piston 25 will remain in its fully actuating position (FIGS. 4 and 5) but then as the diameter of the cam reduces, the piston 25 will begin to retract back to its fully retracted position shown in FIGS. 2 and 3 under the action of the spring 26.

The cams 11-20 are designed so as to move to their actuating positions in a predetermined sequence so that the blisters 62 are ruptured in the same predetermined sequence corresponding to the desired sequence of actions for a particular assay. All actuations required for an assay are done through a single rotation of the cam shaft with all pistons returning to their retracted positions after a single full turn under the action of the spring 26.

Figure 4:
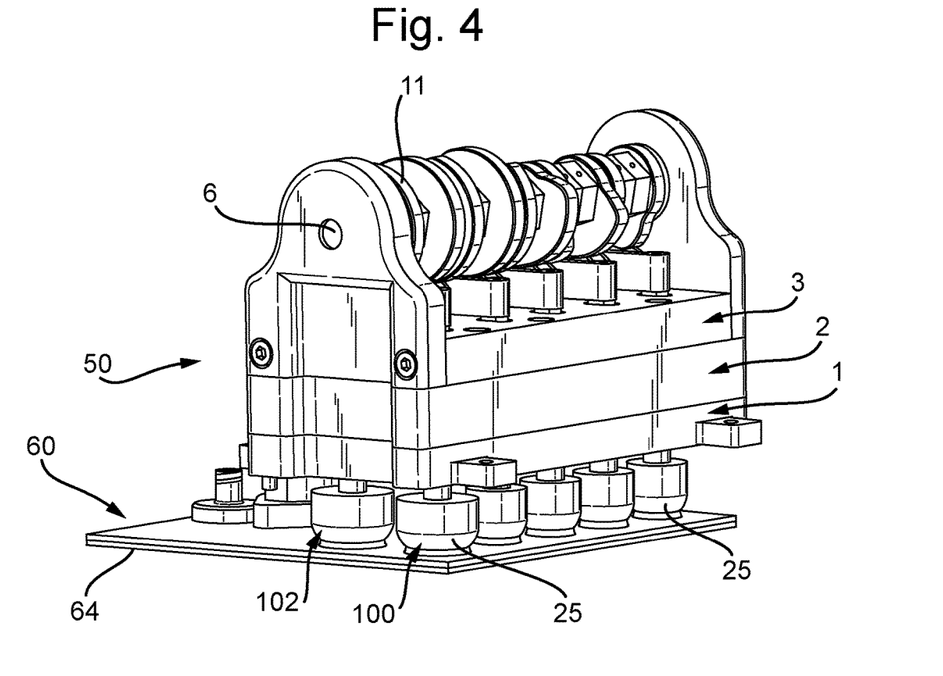
FIG. 4 is a perspective view similar to FIG. 2 but showing the actuators in their actuating positions.
Figure 5:
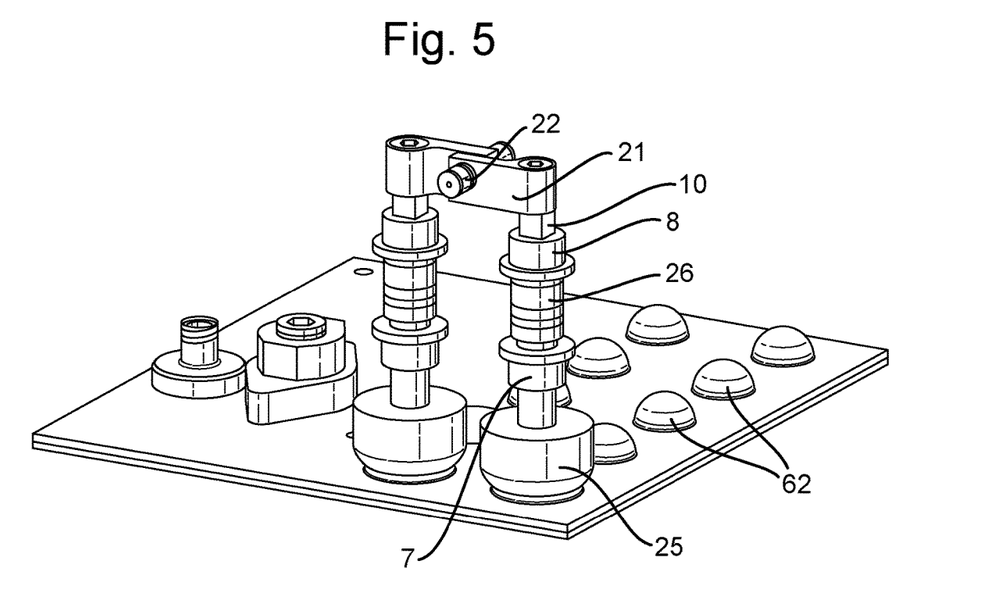
FIG. 5 is a view similar to FIG. 3 but with the actuators in their actuating positions.

As can be seen in FIG. 2 and FIG. 4, the piston assemblies are arranged in two parallel rows 100, 102 with five piston assemblies in each row, which are equally spaced apart along the rows. Pairs of piston assemblies, one from each row, are arranged opposite one another. The piston connector 21 of each piston assembly extends laterally inward from the respective piston rod 10, the piston connectors of the piston assemblies of row 100 being interleaved with the piston connectors of the piston assemblies of row 102.

Interleaving of the piston connectors 21 of each piston assembly is achieved because each piston connector extends outwardly from the respective piston rod 10 from a point that is offset from a central longitudinal axis of said piston rod 10 (i.e. to form a "p" shape at the top of the respective piston rod). As a result, the piston connectors 21 from opposite rows 100, 102 are arranged in pairs. The cams are arranged in corresponding pairs.

As noted above, each piston connector 21 carries a cam follower 22. These are carried on the axially outward facing surfaces of each piston connector pair of the respective interleaved pair of piston assemblies.

Whilst each cam only actuates a single piston assembly, it would of course be possible for one or more cams to actuate multiple piston assemblies simultaneously. This could be achieved by connecting two or more piston assemblies or by multiple piston assemblies having their respective cam followers aligned with the one cam. The latter arrangement is possible through a number of arrangements, such as by having aligned cam followers (not shown).

If a cam and yoke system such as that disclosed in US-A-2012/0168305 were to be used, it would be more difficult to have multiple piston assemblies actuated by a single cam as multiple yokes would need to be fitted round a single cam. As such, a further advantage over the cam and yoke system disclosed in US-A-2012/0168305 is that more of the periphery of each cam is available for actuation and movement of fluids rather than retracting to a start position. This decreases the size of the assembly and increases the time available for actuation and speed range (and therefore accuracy and precision) available for actuation.

By using the relative arrangement of the cam follower, piston connector and piston rod for each piston assembly, the cam shaft 6 is able to be located overhead (i.e. above the piston assemblies) and in an laterally offset position from the rows 100, 102 of piston assemblies. In other words, from above the cam shaft is parallel to, and equidistant from, each row 100, 102 of piston assemblies, and so is located between the two rows of piston assemblies; from the side, it can be seen that the cam shaft is positioned above the piston assemblies so that only the peripheries of the cams are at a similar elevation to the piston assemblies.

Figure 7:
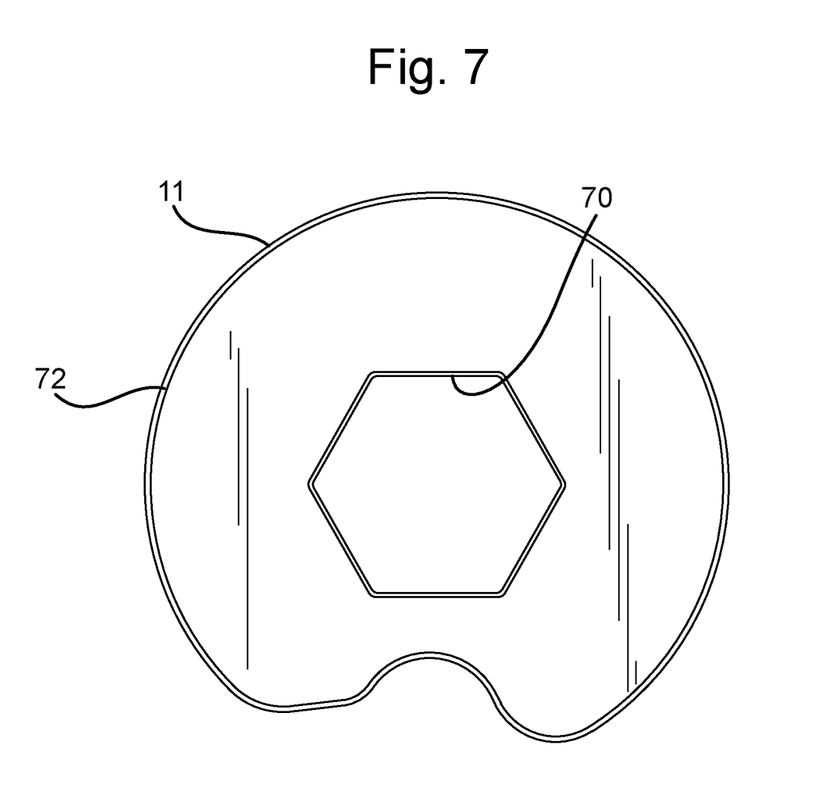

An example of the change in position of a piston as a cam rotates in set out in Table 1 below based on the cam profile shown in FIG. 7. This Table indicates how, starting from a fully retracted position (0 mm) the piston moves through a total of 6 mm following rotation of the cam shaft in response to 1400 steps of the stepper motor. This corresponds to anti-clockwise rotation of the cam shown in FIG. 7.

TABLE 1

| Motor Steps (arb) | 0 | 200 | 400 | 600 | 800 | 1000 | 1200 | 1400 |
|---|---|---|---|---|---|---|---|---|
| Piston Position (mm) | 0 | 2.5 | 3.5 | 4.3 | 4.9 | 5.4 | 5.8 | 6 |

An example of the sequence of actuations of the blisters 62 is set out in Table 2 below. The first blister is indicated to be burst at a time t=0 as a result of rotation of the cam 11 to cause a corresponding piston 25 to move to its actuating position. Thereafter, continued rotation of the cam shaft 6 causes the cams to rotate and hence the corresponding pistons 25 to move linearly towards their actuating positions such that actuation and hence bursting of the corresponding blisters occurs at the times indicated in Table 2. Thus, blister 62-2 will be burst after 60 seconds from the time at which blister 62-1 is burst, blister 62-3 will be burst 1260 seconds after blister 62-1 and so on. Blisters 62-9 and 62-10 are burst at the same time and thus the cams 19, 20 have the same profile.

Following the bursting of blisters 62-9 and 62-10, continued rotation of the cam shaft 6 allows the pistons to return to their retracted positions.

TABLE 2

| Sequence | Cam Number | Reservoir Number (of blisters 62) | Approx. Time (s) |
|---|---|---|---|
| 1 | 11 | 62-1 | 0 |
| 2 | 12 | 62-2 | 60 |
| 3 | 13 | 62-3 | 1260 |
| 4 | 14 | 62-4 | 1300 |
| 5 | 15 | 62-5 | 1350 |
| 6 | 16 | 62-6 | 1375 |
| 7 | 17 | 62-7 | 1400 |
| 8 | 18 | 62-8 | 1500 |
| 9 | 19 + 20 | 62-9 + 62-10 | 1530 |

In addition to activating blisters 62 containing fluid, one or more of the pistons can be used to depress a flexible wall of one of the fluid channels so as to pump fluid onwards through that channel. The speed of pumping can be varied by varying the rotational speed of the motor 27. This will change the rate at which fluid is delivered to the required target.

In some embodiments, the sequence in which the cams move the actuators to their actuating positions has a portion in which all the actuators are simultaneously in their actuating positions. In these cases, when the cams are rotated in one direction (whether in a stepped or smooth manner) the actuators are moved to their respective actuating positions in a predetermined sequence. Then, upon further rotation of the cam shafts, and following the point at which all the actuators are simultaneously in their actuating positions, the actuators all move to their retracted positions simultaneously due to the profile of the cams.

One advantage of these embodiments is that, due to the "sprung" nature of the piston assemblies, should the direction of rotation of the cams be reversed at any time (i.e. to continuously rotate in the opposite direction), a fast and precise "pumping" motion can be instigated. This is possible because the actuators will all pass through their retracted positions and then their (fully) actuated positions simultaneously causing a sudden surge of fluid to be delivered into the channel structure from the fluid reservoirs.

The speed of any pumping motion of the piston assemblies (whether instigated by all the actuators simultaneously or in sequence) is also able to be high as instead of using a clutch mechanism to operate one or more cams (as is disclosed in US-A-2012/0168305 and U.S. Pat. No. 5,073,343), all the cams are rotated when the single cam shaft 6 is rotated As mentioned above, instead of bursting blisters or pumping fluids, the pistons could also be used to drive a syringe to transport fluid from a rigid container towards a target.

The invention claimed is:

1. An assay fluid delivery system comprising an array of fluid reservoirs, each of which is selectively actuatable to deliver a respective fluid to a fluid channel structure; and
a fluid delivery control system comprising two lines of reciprocally mounted actuators in a rectilinear arrangement, each associated with a respective reservoir and being movable between a retracted position and an actuating position at which it causes fluid to be delivered from the corresponding reservoir, a plurality of cams with different profiles mounted on a common, rotatable cam shaft located between the two lines co as and configured to allow both lines of actuators to be engaged by the plurality of cams, each cam being engaged with a respective one of the actuators whereby rotation of the cams is configured to cause movement of the corresponding actuators between the retracted and actuating positions, and a motor coupled to the cam shaft for rotating the cam shaft, wherein the cams are shaped relative to one another so as to cause the corresponding actuators to actuate the reservoirs in a predetermined sequence and for predetermined respective times.

2. A system according to claim 1, wherein at least one cam is shaped to cause increasing pressure to be applied to the corresponding reservoir after fluid commences flowing from that reservoir.

3. A system according to claim 1, wherein the motor is adapted to operate continuously.

4. A system according to claim 1, wherein the cams are shaped so that after actuation, each actuator remains in its actuating position until the last actuator is actuated.

5. A system according to claim 1, wherein each actuator is urged towards its retracted position, for example by a spring.

6. A system according to claim 1, wherein the actuators are detachable.

7. A system according to claim 1, wherein the actuators comprise pistons.

8. A system according to claim 1, wherein the fluid reservoirs comprise one or more of blister packs, partially rigid and rigid chambers.

9. A system according to claim 8, wherein the fluid reservoirs are formed in a blister pack, the fluid channel structure being bonded or otherwise secured to the blister pack.

10. A system according to claim 1, wherein different fluids are contained in the different reservoirs.

11. A system according to claim 1, wherein the fluid channel structure includes at least one fluid channel with a flexible wall part, the control system including an actuator and corresponding cam for flexing the wall part to assist fluid flow along the fluid channel.

12. A system according to claim 1, wherein the system is adapted to carry out one of an immunoassay, molecular, food or toxicology diagnostics assay.

13. A fluid delivery control system for use in an assay fluid delivery system according to any of the preceding claims, the fluid delivery control system comprising two lines of reciprocally mounted actuators in a rectilinear arrangement, each associated with a respective reservoir and being movable between a retracted position and an actuating position at which it causes fluid to be delivered from the corresponding reservoir, a plurality of cams with different profiles mounted on a common, rotatable cam shaft located between the two and configured to allow both lines of actuators to be engaged by the plurality of cams, each cam being engaged with a respective one of the actuators whereby rotation of the cams is configured to cause movement of the corresponding actuators between the retracted and actuating positions, and a motor coupled to the cam shaft for rotating the cam shaft, wherein the cams are shaped relative to one another so as to cause the corresponding actuators to move to the actuated position in a predetermined sequence and for predetermined respective times.

* * * * *